(12) United States Patent
Regensburger et al.

(10) Patent No.: US 12,390,173 B2
(45) Date of Patent: Aug. 19, 2025

(54) HISTOTRIPSY WATER BATH SENSORS TO CHECK REGISTRATION AND METHODS THEREOF

(71) Applicant: Siemens Healthcare GmbH, Erlangen (DE)

(72) Inventors: Alois Regensburger, Poxdorf (DE); James Scheuermann, Malden, MA (US)

(73) Assignee: Siemens Healthineers AG, Forchheim (DE)

( * ) Notice: Subject to any disclaimer, the term of this patent is extended or adjusted under 35 U.S.C. 154(b) by 294 days.

(21) Appl. No.: 18/195,270

(22) Filed: May 9, 2023

(65) Prior Publication Data

US 2024/0081754 A1   Mar. 14, 2024

Related U.S. Application Data

(60) Provisional application No. 63/404,737, filed on Sep. 8, 2022.

(51) Int. Cl.
| | |
|---|---|
| *A61B 6/00* | (2024.01) |
| *A61B 6/03* | (2006.01) |
| *A61B 8/00* | (2006.01) |
| *G06T 11/00* | (2006.01) |

(52) U.S. Cl.
CPC ............ *A61B 6/032* (2013.01); *A61B 6/4441* (2013.01); *A61B 8/4218* (2013.01); *G06T 11/005* (2013.01); *G06T 2207/10081* (2013.01)

(58) Field of Classification Search
CPC .. A61N 2007/0091; A61N 7/00; A61B 6/487; A61B 6/4441; A61B 6/4405; A61B 6/4085
See application file for complete search history.

(56) References Cited

U.S. PATENT DOCUMENTS

| | | | |
|---|---|---|---|
| 2022/0370025 A1 | 11/2022 | Regensburger et al. | |
| 2023/0218930 A1* | 7/2023 | Stopek | A61B 8/085 601/3 |

OTHER PUBLICATIONS

WO2021/258007 (Stopek) (Year: 2021).*

(Continued)

*Primary Examiner* — Dani Fox
(74) *Attorney, Agent, or Firm* — Lempia Summerfield Katz LLC

(57) ABSTRACT

Systems and methods for image-based guidance for ultrasound intervention are provided. The system may include: an imaging device (e.g., an X-ray device, a Computed Tomography (CT) device, or a Magnetic Resonance Tomography (MRT) device) for generating an image dataset of an object of the intervention; an ultrasound transducer for generating ultrasound waves, the ultrasound transducer being mounted to a stand and/or a robot; a basin containing a liquid coupling composition for improving the transmission of ultrasound waves generated by the transducer to the object of the intervention; and a liquid level determining arrangement for determining a liquid level of the coupling composition in the basin. The liquid level determining arrangement may include a mechanical sensor, an electrical sensor, an acoustic sensor, an optical sensor, a camera, a floater, a scale, a visible marking, or a combination thereof.

19 Claims, 4 Drawing Sheets

(56) References Cited

OTHER PUBLICATIONS

Hunter, Allison K., and W. D. McDavid. "Characterization and correction of cupping effect artefacts in cone beam CT." Dentomaxillofacial Radiology 41.3 (2012): 217-223.
Xiaolin Huang et al. "Truncation Artifact Reduction in Cone-beam CT using Mixed One-bit Compressive Sensing," The 14th International Meeting on Fully Three-Dimensional Image Reconstruction in Radiology and Nuclear Medicine 246 Jun. 2017. pp. 1-4.

\* cited by examiner

HISTOTRIPSY WATER BATH SENSORS TO CHECK REGISTRATION AND METHODS THEREOF

The present patent document claims the benefit of U.S. Provisional Patent Application No. 63/404,737, filed Sep. 8, 2022, which is hereby incorporated by reference in its entirety.

TECHNICAL FIELD

The present disclosure relates to systems and methods for image-based guidance in ultrasound imaging interventions. Specifically, the disclosure relates to liquid level determining arrangements (e.g., sensors) within a histotripsy fluid basin that are configured to be used to check registration, detect breathing motion, or assist in correcting artifacts in cone beam computed tomography (CBCT) reconstruction.

BACKGROUND

Histotripsy relates to a non-invasive tissue ablation technology guided by real-time imaging. Using focused ultrasound delivered from outside the body, histotripsy mechanically destroys tissue through cavitation. Histotripsy has also been shown to stimulate an immune response and induce abscopal effects in animal models, which may have positive implications for future cancer treatment. Histotripsy has been investigated for a wide range of applications in pre-clinical studies, including the treatment of cancer, neurological diseases, and cardiovascular diseases.

Challenges with current histotripsy interventions include addressing the breathing motion of the patient during the histotripsy delivery.

Additionally, before a histotripsy treatment, a Cone Beam Computed Tomography (CBCT) scan (or a computed tomography (CT) or magnetic resonance tomography (MRT) scan of the anatomy is acquired (see, e.g., FIG. 1).

In such a scan, a water basin is placed on top of the patient. A fluid (e.g., water) within the water basin is later used to provide ultrasound wave coupling between histotripsy therapy transducer and the patient anatomy. The challenge with this process is that there is a danger of system or patient movements between the CBCT scan and the histotripsy therapy application, which might result in the treatment of wrong parts of the anatomy (e.g., treatment of unintended parts, as well as non-treatment of intended parts such as a part of the tumor).

Movement of the patient before or during histotripsy treatment may be further complicated when treating deep anatomic locations (e.g., in the pancreas), which are too far away from the histotripsy imaging transducer to monitor the anatomy with live ultrasound imaging. The therapy transducer has lower frequencies than imaging transducers and is therefore able to treat at deeper locations than are visible for imaging ultrasound at higher frequencies. It would be desirable to fully rely on the registration to a previous CBCT scan, and not have to perform additional imaging to provide registration throughout the therapy.

These challenges with patient motion (e.g., breathing motion) are addressed in the current state of the art by identifying and planning an ablation zone treatment area or zone that is smaller than needed to treat the affected area. The breathing motion effectively increases the size of the treatment zone. The use of real-time imaging for motion detection and compensation is also known. Further, through real-time imaging and monitoring, care may be taken to identify when changes or movements take place and adjust treatment accordingly.

An additional challenge with the current state of the art include challenges in the registration between histotripsy therapy transducer (e.g., positioned by a robot having a robot coordinate system) and the CBCT coordinate system. This may be addressed by conducting an additional CT scan of a registration reference object held by a robotic arm, which results in additional step of workflow, additional effort for medical personnel, and additional source of potential errors.

Further, water basins in histotripsy treatments may cause additional truncation and cupping artifacts in the CBCT reconstruction. Specifically, insufficient information about the water basin and its water filling level may lead to truncation and cupping artifacts. In the current state-of-the-art, there is no known solution beyond standard algorithms for artifact correction. As such, a solution to this problem may have the potential to significantly improve CBCT image quality in image guidance for histotripsy. In other words, truncation and cupping artifacts may be reduced or eliminated with information about the shape and fluid level within the basin.

An additional challenge or problem with histotripsy treatments includes deformation of inner soft tissue organs. Specifically, when inserting a histotripsy transducer into the water basin, the water level will change, and thereby change the amount of force of the water basin acting on the body, which can potentially adversely affect or deform the soft tissue organs.

Cupping artifacts are explained in the scientific publication: "Characterization and correction of cupping effect artefacts in cone beam CT," AK Hunter and WD McDavid, Dentomaxillofac Radiol., March 2012, Vol. 41(3), pp. 217-223.

Truncation is explained in the scientific publication: "Truncation Artifact Reduction in Cone-beam CT using Mixed One-bit Compressive Sensing," Xiaolin Huang et al, The 14th International Meeting on Fully Three-Dimensional Image Reconstruction in Radiology and Nuclear Medicine 246 June 2017, Xi'an.

SUMMARY

The scope of the present disclosure is defined solely by the appended claims and is not affected to any degree by the statements within this summary. The present embodiments may obviate one or more of the drawbacks or limitations in the related art.

In one embodiment, a system for image-based guidance for an ultrasound intervention is provided. The system includes an imaging device configured to generate an image dataset of an object of the ultrasound intervention; an ultrasound transducer configured to generate ultrasound waves; a fluid basin comprising a liquid coupling composition configured to improve transmission of ultrasound waves generated by the ultrasound transducer to the object of the ultrasound intervention; and a liquid level determining arrangement configured to provide a liquid level of the liquid coupling composition in the fluid basin.

The imaging device may be an X-ray device, a Computed Tomography (CT) device, or a Magnetic Resonance Tomography (MRT) device.

The system may further include a stand and/or a robot, wherein the ultrasound transducer is mounted to the stand and/or the robot.

The liquid level determining arrangement may include a mechanical sensor, an electrical sensor, an acoustic sensor, an optical sensor, a camera, a floater, a scale, a visible marking, or a combination thereof.

The system may further include an image processing unit configured to receive the image dataset from the imaging device. The image processing unit may include an interface configured to receive a liquid level signal determined by the liquid level determining arrangement. The image processing unit may be configured to determine a correction value for one or more pixel values or voxel values of the image dataset based on the liquid level signal, wherein the one or more pixel values or voxel values generated by the imaging device have been influenced by the liquid coupling composition.

In certain examples, the imaging device may be an X-ray device or a Computed Tomography device, and the correction value may be configured to compensate for a truncation artifact, a cupping artifact, a value offset, or a combination thereof caused by X-ray having passed through the liquid coupling composition.

In another embodiment, a method for image-based guidance of an ultrasound intervention is provided. The method includes generating, by an imaging device, an image dataset of an object of the ultrasound intervention. The method further includes generating ultrasound waves by an ultrasound transducer positioned in a fluid basin comprising a liquid coupling composition, wherein the liquid coupling composition is provided to assist in a transmission of the ultrasound waves generated by the ultrasound transducer to the object. The method further includes determining, by a liquid level determining arrangement, a liquid level of the liquid coupling composition in the fluid basin having the ultrasound transducer positioned in the fluid basin.

Within the method, the imaging device may be an X-ray device, a Computed Tomography (CT) device, or a Magnetic Resonance Tomography (MRT) device.

In certain examples, the ultrasound transducer may be mounted to a stand and/or a robot.

In certain examples, the liquid level determining arrangement may include a mechanical sensor, an electrical sensor, an acoustic sensor, an optical sensor, a camera, a floater, a scale, a visible marking, or a combination thereof.

In certain examples, the method further includes: receiving, by an image processing unit, an image dataset from the imaging device; receiving, by the image processing unit, a liquid level signal determined by the liquid level determining arrangement; and determining, by the image processing unit, a correction value for one or more pixel values or voxel values of the image dataset based on the liquid level signal, wherein the one or more pixel values or voxel values generated by the imaging device have been influenced by the liquid coupling composition.

The imaging device may be an X-ray device or a Computed Tomography device, and the correction value may be configured to compensate for a truncation artifact, a cupping artifact, a value offset, or a combination thereof caused by X-ray having passed through the liquid coupling composition.

In other examples, the method may include: determining, by the liquid level determining arrangement, an initial liquid level of the liquid coupling composition in the fluid basin, prior to positioning the ultrasound transducer in the fluid basin; and identifying a change in the liquid level based on a difference between the initial liquid level and the liquid level having the ultrasound transducer positioned in the fluid basin.

In other examples, the method may include: using the identified change in the liquid level for confirmation that a registration of a scan by the imaging device remains correct; and performing a re-registration when the identified change in the liquid level identifies an inconsistency.

In other examples, the method may include: determining a breathing cycle of the object based on the identified change in the liquid level; and using the determined breathing cycle for a motion-compensated histotripsy treatment.

In other examples, the method may include: calculating a deformation force exerted by the fluid basin and the transducer onto the object based on the identified change in the liquid level; and estimating a deformation on inner soft tissue anatomy of the object based on the calculated deformation force.

In other examples, the method may include: adjusting a depth of the ultrasound transducer within the fluid basin, wherein the ultrasound transducer is affixed to and controlled by a robot; and determining, by the liquid level determining arrangement, a position of the ultrasound transducer positioned within the fluid basin based on: (1) a known position of the fluid basin, and (2) a change in the liquid level of the liquid coupling composition caused by the adjusting of the depth of the ultrasound transducer.

In additional examples, the method may include registering a robot coordinate system relative to the fluid basin based on the determined position of the ultrasound transducer.

In other examples, the method may include determining a truncation or cupping correction model using the determined liquid level in the fluid basin.

In other examples, the method may include detecting, by the liquid level determining arrangement, a movement of the fluid basin between the generating of the image dataset and the generating of the ultrasound waves.

In another embodiment, a method for image-based guidance of an ultrasound intervention is provided. The method includes: loading a pre-interventional dataset of an object without a fluid basin or with an empty fluid basing having no liquid; calculating virtual projection images using the pre-interventional dataset; comparing attenuation of rays in current projection images to virtual projection rays of the virtual projection images; determining a delta attenuation per projection ray; determining a fluid filling level of the fluid basin by fitting the delta attenuation of multiple projection rays to a position of the fluid basin; and performing a truncation or cupping artifact compensated computed tomography image reconstruction taking into account the position and fluid filling level of the fluid basin.

In another embodiment, a method for image-based guidance of an ultrasound intervention is provided. The method includes: performing multiple preliminary computed tomography reconstructions assuming different fluid filling levels in a fluid basin positioned on a surface of an object of the ultrasound intervention; determining a level of a cupping or truncation artifact by: comparing voxel values of known and segmented tissue regions and calculating differences across the image, or determining a strength of global image brightness variations and shapes caused by the cupping or truncation artifact; iteratively determining a fluid filling level in the fluid basin with lowest appearance of artifacts or voxel value differences of reference objects across the image; and performing a truncation or cupping artifact compensated computed tomography image reconstruction taking into account a position of the fluid basin and the fluid filling level of the fluid basin.

BRIEF DESCRIPTION OF THE DRAWINGS

Exemplary embodiments are described herein with reference to the following drawings.

DETAILED DESCRIPTION

The following disclosure relates to improved liquid level determining arrangements (e.g., sensors) within a histotripsy fluid basin, which are configured to check registration, detect breathing motion, or assist in correcting artifacts in cone beam computed tomography (CBCT) reconstruction.

The improved liquid level determining arrangement (e.g., sensor) may advantageously be used for image guidance using a mobile C-arm x-ray apparatus or a fixed C-arm apparatus for guiding histotripsy treatments. Having a sensor in the fluid basin may provide an important indication whether registration is still correct, therein increasing the safety of treatment delivery and reducing the need of frequent image-based re-registration. Using sensors in the fluid basins for registration of the histotripsy robot to Cone Beam Computed Tomography (CBCT) may make the workflow easier for medical personnel. Moreover, the image quality of the CBCT with the fluid basin in place may be increased significantly by the artifact correction, as described below.

Figure 1:
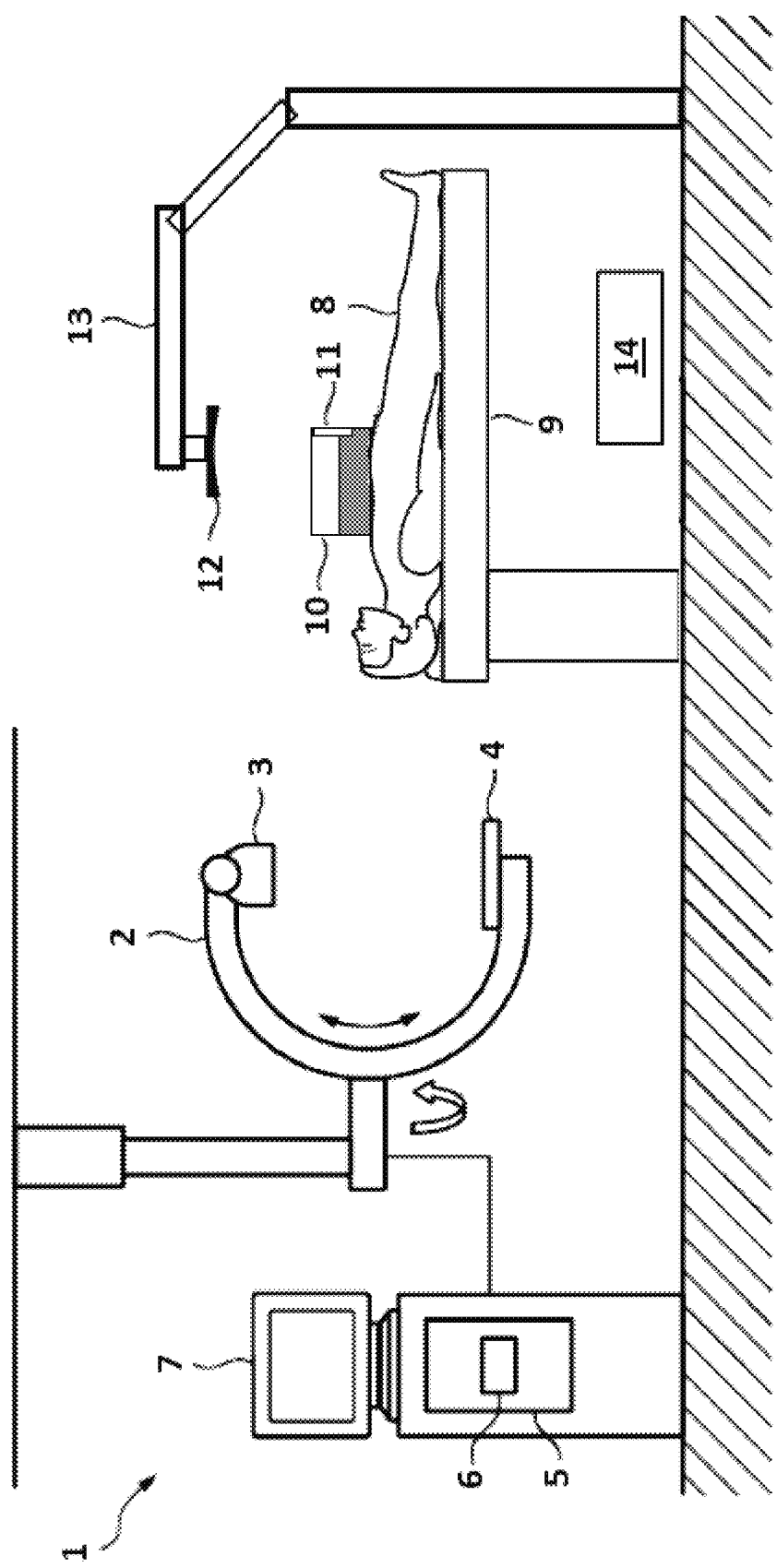
FIG. 1 depicts an example of an imaging arrangement before a histotripsy treatment and during cone beam computed tomography (CBCT) imaging.

FIG. 1 depicts an example of an imaging arrangement before a histotripsy treatment and during cone beam computed tomography (CBCT) imaging. In this arrangement, the figure depicts an example of a C-arm X-ray device 1. Mounted on the C-arm 2 is an X-ray source 3 and a flat-panel X-ray detector 4. The C-arm 2 is configured to rotate around the object under examination and, while doing so, to acquire a series of projection images from different projection directions. Acquisition of this kind with subsequent reconstruction is known, e.g., as cone-beam CT (CBCT) or also DynaCT. The C-arm X-ray device 1 is controlled by a system control unit 5. The C-arm X-ray device also includes a processing unit 6 having at least one processor and software for processing and/or reconstructing images. A display unit 7 is provided for displaying the resulting processed or reconstructed images and all the other images.

As noted above, in such a scan, an object to be examined 8 (e.g., a patient) is positioned on top of or supported by an examination table 9. Additionally, a fluid (e.g., water) basin 10 has been positioned on top of a patient 8. The fluid basin 10 will later be used to ensure ultrasound wave coupling between histotripsy therapy transducer and the patient anatomy. A fluid height sensor 11 is positioned within the fluid basin 10 to measure the fluid level. Additionally depicted within FIG. 1 is a therapy transducer 12, which may be affixed to an end of a robot or robotic positioning device 13 that is configured to move to reposition the transducer within the fluid basin 10. Further, an additional system control unit or processing unit 14 may be associated with the therapy transducer 12 and robotic positioning device 13. Alternatively, the system control unit 5 and processing unit 6 associated with the C-arm X-ray device 1 may also be configured to control the therapy transducer 12 and robotic positioning device 13.

The problem with this arrangement is that there is a danger of system or patient movements between CBCT scan and histotripsy therapy application, which might result in the treatment of wrong parts of the anatomy (e.g., treatment of unintended parts, as well as non-treatment of intended parts such as a part of the tumor).

Figure 2:
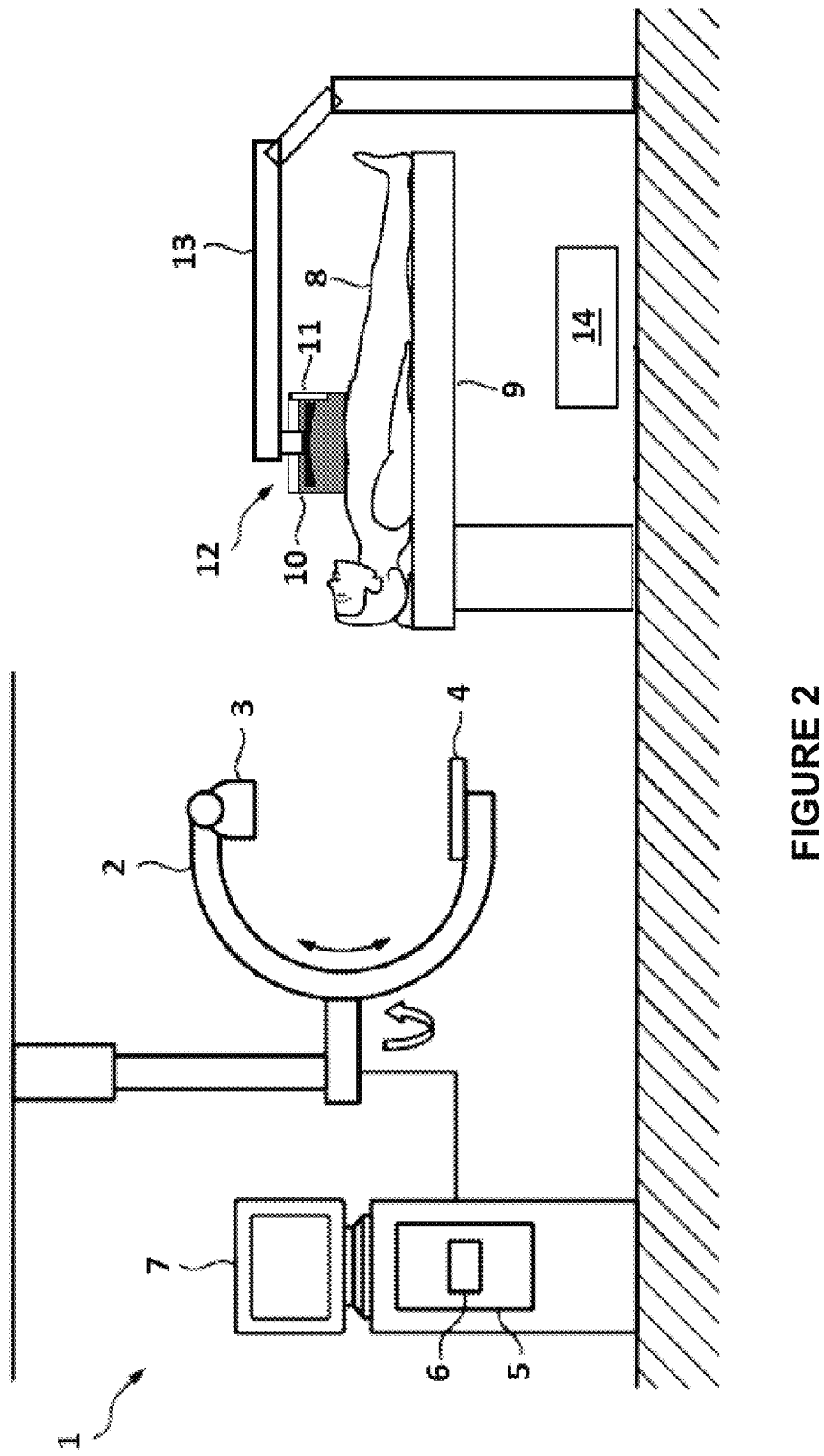
FIG. 2 depicts an example of an improved histotripsy therapy application.

FIG. 2 depicts an example of an improved histotripsy therapy system that may address these concerns. The system may include an imaging device 1 configured to generate an image dataset of an object of the ultrasound intervention (e.g., the patient).

The imaging device may be an X-ray device, a Computed Tomography (CT) device, or a Magnetic Resonance Tomography (MRT) device.

In this example in FIG. 2, the imaging device is a C-arm X-ray device 1. Mounted on the C-arm 2 is an X-ray source 3 and a flat-panel X-ray detector 4. The C-arm 2 is configured to rotate around the object under examination and, while doing so, to acquire a series of projection images from different projection directions. Acquisition of this kind with subsequent reconstruction is known, e.g., as cone-beam CT (CBCT) or also DynaCT. The C-arm X-ray device 1 is controlled by a system control unit 5. The C-arm X-ray device also includes a processing unit 6 having at least one processor and software for processing and/or reconstructing images. A display unit 7 is provided for displaying the resulting processed or reconstructed images and all the other images.

In this embodiment depicted in FIG. 2, the histotripsy therapy delivery system may include a therapy ultrasound transducer 12. The system may further include a robot or robotic positioning device 13 configured to position the therapy ultrasound transducer 12. In the example depicted in FIG. 2, the transducer 12 is positioned in the fluid of the fluid basin 10, causing the fluid level to rise (as compared to the fluid level in FIG. 1 without the transducer positioned within the fluid).

Additionally, the histotripsy therapy delivery system may include an imaging system having three-dimensional (3D) acquisition capability. Examples of such 3D systems may include C-arm, CT, or MRT imaging systems. As depicted in FIG. 2, the imaging system is a C-arm system. While other systems such as CT or MRT systems may be included, the following description will relate to a C-arm system acquiring a CBCT.

As depicted in FIG. 2, an object to be imaged 8 (e.g., a patient) may be positioned on an examination table 9. A fluid (e.g., water) basin 10 may be positioned on the surface of the patient 8. The fluid basin 10 may be configured to provide wave coupling between therapy transducer and patient anatomy.

In certain examples, the fluid basin 10 may include markers or identifiers (e.g., X-ray visible markers) that are positioned in a known geometry.

The fluid basin 10 may be filled (e.g., partially filled less than the entire volume of the basin) with a liquid coupling composition, fluid, or gel-like substance. The liquid coupling composition may be configured to improve transmission of ultrasound waves generated by the ultrasound transducer to the object of the ultrasound intervention. In certain examples, the liquid coupling composition or fluid is water.

The fluid basin 10 may be fixed to the surface of the patient 8, (e.g., via straps) to advantageously reduce movement between the fluid basin and patient 8.

In certain examples, a liquid level determining arrangement or sensor 11 may be positioned within the fluid basin 10, such as adjacent to an internal wall/surface of the basin. Alternatively, the liquid level determining arrangement or sensor 11 may be positioned outside of the fluid basin 10, such as adjacent to an external wall/surface of the basin 10.

The sensor 11 may be configured to monitor or measure the liquid/fluid level or height within the basin 10. Additionally, or alternatively, the sensor 11 may be configured to measure or monitor the fluid/gel motion or waves within the basin 10.

The liquid level determining arrangement or sensor 11 may be a mechanical sensor, an electric sensor, an acoustic sensor, or ultrasound sensor. In other examples, the liquid level determining arrangement or sensor may be an optical camera, reflector, or floater configured to measure the fluid/gel height and/or motion/waves within the basin. In certain examples, the liquid level determining arrangement or sensor 11 may not measure a specific or absolute height of the fluid/gel within the basin. Instead, the liquid level determining arrangement or sensor 11 may be configured to identify or measure a relative height or relative position information. In such cases, the liquid level determining arrangement or sensor 11 may be configured to identify a change (rise or fall) in the fluid level and identify the relative change in height. In other words, while the absolute height of the starting or ending fluid level may not necessarily be identified by one of the nonlimiting examples of sensors described herein, the sensor may still be able to identify a change in height of the fluid using a relative starting and ending height measurements.

In certain examples, the fluid basin 10 may include at least one scale to identify the fluid (e.g., water) level within the basin 10. The scale may be configured to be manually read by a user/operator or a camera may be configured to monitor and/or read the scale. The scale may be identified by centimeter, millimeter, or inch scale, or any other visible marking configuration. The scale may be positioned on one surface/wall (e.g., internal or external wall) of the fluid basin 10. In some examples, the at least one scale may include two scales positioned on opposite sides/walls of the fluid basin 10.

The system may further include one or more data or imaging processing units 6. The processing unit 6 may be configured to receive an image dataset from the imaging device 1. The imaging processing unit 6 may include an interface configured to receive a liquid level signal determined by the liquid level determining arrangement 11. In some examples, the liquid level signal(s) received by the imaging processing unit 6 may provide a relative change in height of the fluid level within the basin.

In certain examples, the imaging processing unit 6 may be configured to determine a correction value for one or more pixel values or voxel values of the image dataset based on the liquid level signal(s) (e.g., a relative change in height of the fluid level), wherein the one or more pixel values or voxel values generated by the imaging device have been influenced by the liquid coupling composition.

In some examples, the imaging device 1 is an X-ray device or a Computed Tomography device, and the correction value is configured to compensate for a truncation artifact, a cupping artifact, a value offset, or a combination thereof caused by X-ray having passed through the liquid coupling composition.

In certain examples, the liquid or fluid level (or change in the fluid level) may be entered (e.g., by a user) or otherwise provided by a computer operated reading to the imaging processing unit configured to perform a truncation-corrected image reconstruction. In the embodiment in which there are two scales present within the basin, and two separate readings, the truncation correction may be configured to identify a tilt in the fluid basin based on the two readings provided to the image processing unit.

As depicted in FIG. 2, the system may include one or more system control units 5, 14. The control unit 5, 14 may be configured to control the robot for positioning the therapy transducer 12. Additionally, or alternatively, the control unit 5, 14 may be configured to control the imaging system (e.g., the C-arm imaging system). Further, the control unit 5, 14 may be configured to control the wave coupling between therapy transducer and patient anatomy. In some examples, the control unit 5, 14 may be in communication with the liquid level determining arrangement or sensor to monitor or measure the fluid/gel (e.g., water) height and/or the fluid/gel motion or waves within the basin. The control unit 5, 14 may be in communication with a camera configured to read the at least one scale of the fluid basin. In certain examples, the height measurements of the fluid within the basin may be relative measurements, wherein a relative change in the fluid height within the basin, for example, is identified by the sensor and transmitted to the control unit for further processing.

Additionally, or alternatively, the control unit 5, 14 may be in communication with the data or image processing unit to perform the truncation-corrected image reconstruction, e.g., using the measured fluid level or identified relative change in height of the fluid level.

Figure 3:
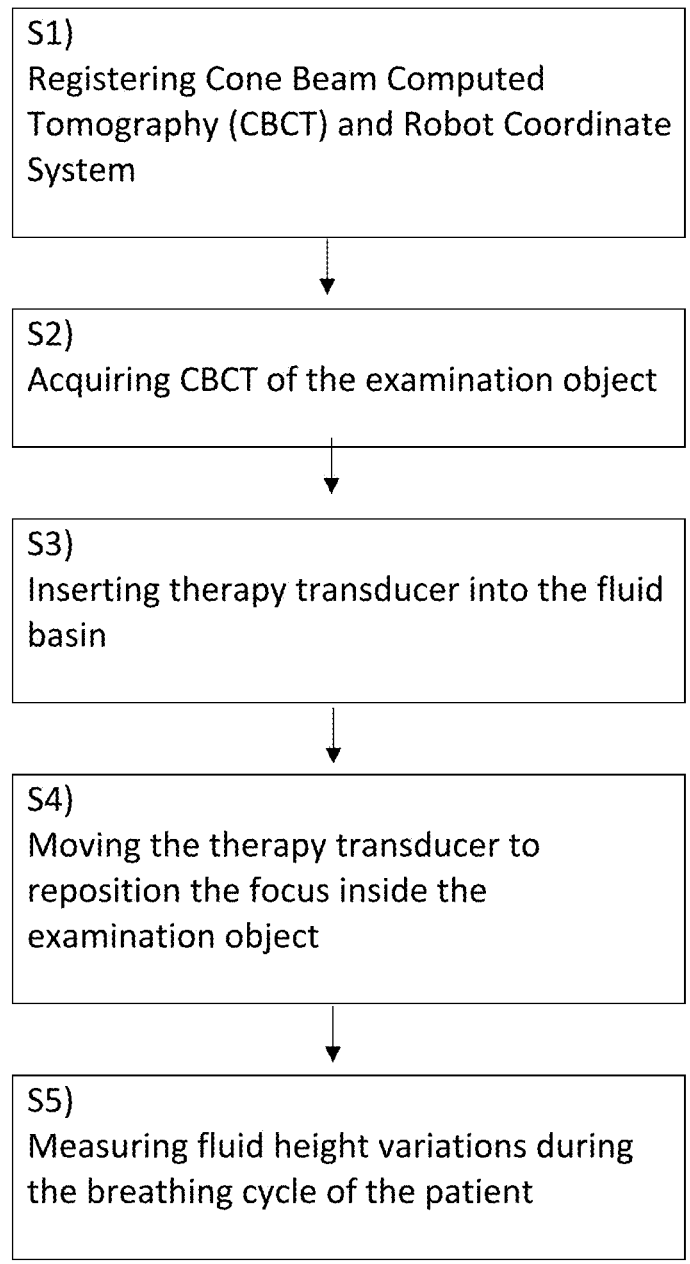
FIG. 3 depicts an exemplary method of a histotripsy therapy application.

FIG. 3 depicts a method for carrying out a histotripsy therapy application. In act S1, a registration between the CBCT and robot coordinate system may be conducted, (e.g., by scanning therapy transducer or reference object mounted to robot).

In act S2, a CBCT of the examination object (e.g., patient) is acquired, wherein the fluid basin is already in position on the surface of the object/patient. In some examples, the location or position of the fluid basin on the surface of the patient is known, and the known position is input into the positioning system for further processing. In certain examples, the location of the fluid basin, and optionally the shape of the fluid/patient surface are determined in the scan.

The height of the fluid (e.g., water) level during the scan may be determined by the signal of the liquid level determining arrangement (e.g., water height sensor), and/or, if possible, from image data. In certain examples, the absolute height of the fluid level is not necessarily determined. Instead, a relative height of the fluid level may be identified based on the properties identified by the liquid level determining arrangement or sensor.

In act S3, when the therapy transducer is (e.g., slowly) inserted by the robot into the fluid basin, fluid (e.g., water) will be displaced, and the fluid level will rise. The dynamics of this rise in fluid height are registered by the liquid level determining arrangement/sensor and used to check for registration accuracy. In certain examples, as noted above, the liquid level determining arrangement or sensor may be configured to measure or identify a relative change in height of the fluid within the basin. That is, while the absolute starting height or absolute ending height may not be identified, the relative change in height may be measured by the sensor. In the case where there are inconsistent fluid height readings detected, a warning is output to the user, prompting the user to perform a re-registration.

In act S4, in examples where the therapy transducer has a fixed ultrasound focal length, during the histotripsy therapy application, the therapy transducer is moved by the robot to reposition the focus inside the examination object. Moving the therapy transducer up or down inside the fluid basin may change the fluid height. This change may be measured by the liquid level determining arrangement or sensor and used for an additional verification that registration is still correct. In some examples, multiple measurements by the liquid level determining arrangement or sensor may be combined to calculate an average measurement that compensates for breathing effects of the patient. In certain examples, when inconsistencies are identified, the user is prompted to perform a re-registration.

In act S5, during the histotripsy therapy treatment, fluid (e.g., water) height variations may be measured to determine the breathing cycle of the patient. This may be used as input for motion-compensated histotripsy treatment.

In other words, when the patient breathes in and out, the basin positioned on the patient's body (e.g., chest) is lifted and lowered. When the basin is lifted during the patient's breathing cycle, the ultrasound probe may be submerged deeper into the fluid within the basin. Further, when the basin is lowered during the patient's breathing cycle, the ultrasound probe may at least partially emerge from the fluid within the basin. Through the submerging and emerging of the probe within the fluid of the basin, the liquid level in the basin will rise and drop, respectively. The measuring of the variations in the fluid height via the rising and dropping of the liquid level may thus be an indicator of the breathing motion of the patient, and therefore may be used for motion compensation of the registration.

Figure 4:
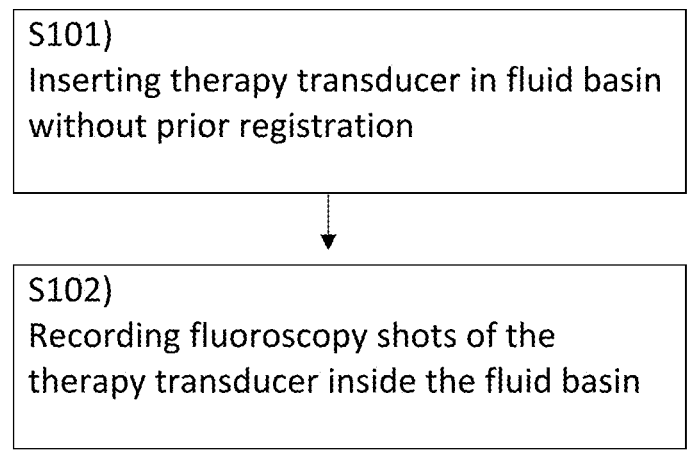
FIG. 4 depicts an exemplary method of a histotripsy therapy application.

In another embodiment, the liquid level determining arrangement or sensor may be configured for registration of the robot. This embodiment may be advantageous in avoiding having to perform an additional CBCT scan of the robot to register the robot coordinate space to the CBCT coordinates (therein avoiding having to perform act S1 as described above). FIG. 4 depicts an example of this embodiment.

In the method depicted in FIG. 4, in act S101, without prior registration, the therapy transducer held by the robot may be manually placed in the fluid basin (e.g., water tank). Changes of fluid height and measurements of fluid displacement may be registered by the sensor and may be later used as a check or verification of registration (at least in vertical direction).

In act S102, at least two fluoroscopy shots of the therapy transducer inside the fluid basin may be recorded by the C-arm, with X-ray visible fiducials attached to the fluid basin visible in X-ray images.

In certain examples, the fluid basin may include at least one position sensor (e.g., optical distance sensor(s), ultrasonic distance sensor(s), radar distance sensor(s), electromagnetic sensor(s)) configured to determine the position of the therapy transducer within the fluid basin. The determination of the transducer position may involve adjusting the depth of the transducer within the fluid basin. This adjustment may be conducted by a user or operator. Alternatively, transducer may be affixed to and controlled by a robot. Adjusting the depth of the transducer within the fluid basin may change the liquid level. That is, submerging the transducer deeper into the fluid basin will cause the liquid level to rise, while partially removing the transducer from the fluid basin will cause the liquid level to fall. The liquid level determining arrangement or sensor may identify this change in the liquid level. The position of the transducer may be identified using the determined change in the liquid level as well as the defined/known position of the fluid basin itself.

In certain alternative arrangements within this embodiment, the position and pose of the therapy transducer may be determined through multiple movements of the transducer by the robot. Specifically, the robot may make slow and controlled movements of the therapy transducer along three spatial directions (e.g., along x, y, and z-directions), and dynamic changes of the sensor readings and fluid height sensor readings may be recorded. The registration of the robot coordinate system relative to the fluid basin may be determined by evaluating these sensor readings, and optionally the robot movement information.

In another embodiment, the liquid level determining arrangement or sensor associated with the fluid basin may assist in correcting truncation or cupping artifacts in the CBCT reconstruction. Specifically, for correcting truncation and cupping artifacts in CBCT, parts of the examination object (e.g., patient) that are outside of the main reconstruction volume need to be known or assumed, as the fluid level within the fluid basin cannot be determined from a direct image reconstruction because of truncation.

For standard patient treatments, the shape of the patient outside the reconstruction volume is assumed, e.g., as a cylinder or elliptical body. Contrary to the state of the art, in this disclosure, the fluid basin adds an important deviation from such a standard patient model. To add the fluid basin to the truncation correction model, the following aspects are introduced by the current disclosure. For one, X-ray detectable markers, patterns, or shapes that are part of the fluid basin or attached to the fluid basin may be used to reconstruct the position and pose of the fluid basin. Additionally, the sensor may be used to determine the fluid level within the basin. This measured height or measured change in height may then be used to the truncation/cupping correction model.

This is contrary to and an advantageous improvement over the state of the art, as it is difficult to impossible to precisely estimate the height or level of fluid (e.g., water) inside the fluid basin from X-ray projection images. Specifically, because of limited detector size, the available projection rays would not intersect the fluid basin in an angle which makes the fluid level visible. So, this problem is not easily solved with image-based methods, at least not without loading a previous X-ray scan of the patient or adding in some additional assumptions. In other words, using a fluid level sensor for artifact correction may be a very important feature to enable a simplified CBCT-guided histotripsy workflow.

Another option for using the liquid level determining arrangement or sensor associated with the fluid basin to assist in correcting truncation or cupping artifacts in the CBCT reconstruction includes loading a pre-interventional image dataset of the same patient (e.g., a CT dataset) without the fluid basin positioned on the patient or with an empty fluid basing having no liquid, calculating virtual projection images using the pre-interventional dataset, and registering to the initial CBCT reconstruction. The process further includes comparing the attenuation of rays in the current projection images to the virtual projection rays and determining a delta attenuation per projection ray. The process may further include determining a probable fluid level within the fluid basin by fitting the delta attenuation of multiple projection rays to a position of the fluid basin. This determination may assume a horizontal and flat fluid surface on the patient. With these calculations and determinations, the process may further include performing the truncation/ cupping artifact compensated CBCT image reconstruction taking into account the determined position/fluid level of the fluid basin.

In other option, the process may include performing multiple "test-compensated" preliminary CBCT reconstructions assuming different fluid filling levels in the fluid basin in addition to a standard truncation model for the patient. The process may further include determining a level of cupping/truncation artifact by comparing voxel values of known/segmented tissue regions as e.g., blood/organ tissue/bone/reference phantom(s) and calculating differences across the image. The process may further include determining the strength of typical global image brightness variations and shapes caused by the cupping/truncation artifact. The process may further include an iterative act of determining the fluid filling level with lowest appearance of artifacts or voxel value differences of the reference objects across the image. The process may further include performing a truncation/cupping artifact compensated CBCT image reconstruction taking into account the position and filling level of the water basin.

In another embodiment, the monitoring of the fluid level within the fluid basin may advantageously be used to determine a deformation of soft tissue organs within the patient. Specifically, at the time of the imaging (e.g., CBCT scanning), the partially filled fluid basin is already positioned on a surface (top) of the patient. The partially filled fluid basin provides an initial deformation force on the patient, and a resulting initial deformation of the soft tissue organs.

Subsequently, when the histotripsy transducer is inserted into the fluid basin (e.g., by the robot/controller), the fluid (e.g., water) level will rise. At the same time, the insertion of the transducer will additionally exert an additional pressure or deformation force onto the patient. The liquid level determining arrangement or sensor may monitor and identify the change in the fluid level. With this understanding of the fluid level change from the sensor, additional calculations may be made with regard to the resulting deformation force caused by the fluid basin and inserted transducer. Based on this calculated deformation force, the change in the deformation on or within the patient's body may be identified. Specifically, an estimation may be made for the deformation of inner soft tissue anatomy within the patient using one or more numerical methods. For example, a finite element modeling (FEM) may be used.

In another embodiment, the liquid level determining arrangement or sensor may be configured to check or monitor the fluid basin for movement. Specifically, the system having the sensor may be configured to detect whether or not the fluid basin has moved between or during the CBCT acquisition and the histotripsy treatment. This detection may be conducted by the liquid level determining arrangement/sensor positioned on a surface (e.g., internal or external surface) of the fluid basin or within the fluid basin. This may be an optical sensor monitoring the fluid within the fluid basin or X-ray visible features of the fluid basin, potentially in combination with at least one fluoroscopy image. Alternatively, or additionally, a sensor may be positioned on the robotic arm that fixes the fluid basin to the examination table.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the disclosure has been illustrated and described in detail with the help of the embodiments, the disclosure is not limited to the disclosed examples. Other variations may be deduced by those skilled in the art without leaving the scope of protection of the claimed disclosure.

The invention claimed is:

1. A system for image-based guidance for an ultrasound intervention, the system comprising:
   an imaging device configured to generate an image dataset of an object of the ultrasound intervention;
   an ultrasound transducer configured to generate ultrasound waves;
   a fluid basin comprising a liquid coupling composition configured to improve transmission of ultrasound waves generated by the ultrasound transducer to the object of the ultrasound intervention;
   a liquid level determining arrangement configured to provide a liquid level of the liquid coupling composition in the fluid basin; and
   an image processing unit configured to receive the image dataset from the imaging device,
   wherein the image processing unit comprises an interface configured to receive a liquid level signal determined by the liquid level determining arrangement,
   wherein the image processing unit is configured to determine a correction value for one or more pixel values or voxel values of the image dataset based on the liquid level signal, and
   wherein the one or more pixel values or voxel values generated by the imaging device have been influenced by the liquid coupling composition.

2. The system of claim 1, wherein the imaging device is an X-ray device, a Computed Tomography (CT) device, or a Magnetic Resonance Tomography (MRT) device.

3. The system of claim 1, further comprising:
   a stand and/or a robot,
   wherein the ultrasound transducer is mounted to the stand and/or the robot.

4. The system of claim 1, wherein the liquid level determining arrangement comprises a mechanical sensor, an electrical sensor, an acoustic sensor, an optical sensor, a camera, a floater, a scale, a visible marking, or a combination thereof.

5. The system of claim 1, wherein the imaging device is an X-ray device or a Computed Tomography device,
   wherein the correction value is configured to compensate for a truncation artifact, a cupping artifact, a value offset, or a combination thereof caused by X-ray having passed through the liquid coupling composition.

6. A method for image-based guidance of an ultrasound intervention, the method comprising:
   generating, by an imaging device, an image dataset of an object of the ultrasound intervention;
   generating ultrasound waves by an ultrasound transducer positioned in a fluid basin comprising a liquid coupling composition, wherein the liquid coupling composition is provided to assist in a transmission of the ultrasound waves generated by the ultrasound transducer to the object;
   determining, by a liquid level determining arrangement, an initial liquid level of the liquid coupling composition in the fluid basin, prior to positioning the ultrasound
transducer in the fluid basin;
determining, by the liquid level determining arrangement,
a liquid level of the liquid coupling composition in the
fluid basin having the ultrasound transducer positioned
in the fluid basin;
identifying a change in the liquid level based on a
difference between the initial liquid level and the liquid
level having the ultrasound transducer positioned in the
fluid basin; and
performing one of the following:
(1) using the identified change in the liquid level for
confirmation that a registration of a scan by the
imaging device remains correct; and performing a
re-registration when the identified change in the
liquid level identifies an inconsistency; or
(2) determining a breathing cycle of the object based on
the identified change in the liquid level; and using
the determined breathing cycle for a motion-compensated histotripsy treatment; or
(3) calculating a deformation force exerted by the fluid
basin and the ultrasound transducer onto the object
based on the identified change in the liquid level; and
estimating a deformation on inner soft tissue
anatomy of the object based on the calculated deformation force.

7. The method of claim 6, wherein the imaging device is
an X-ray device, a Computed Tomography (CT) device, or
a Magnetic Resonance Tomography (MRT) device.

8. The method of claim 6, wherein the ultrasound transducer is mounted to a stand and/or a robot.

9. The method of claim 6, wherein the liquid level
determining arrangement comprises a mechanical sensor, an
electrical sensor, an acoustic sensor, an optical sensor, a
camera, a floater, a scale, a visible marking, or a combination
thereof.

10. A method for image-based guidance of an ultrasound
intervention, the method comprising:
generating, by an imaging device, an image dataset of an
object of the ultrasound intervention;
generating ultrasound waves by an ultrasound transducer
positioned in a fluid basin comprising a liquid coupling
composition, wherein the liquid coupling composition
is provided to assist in a transmission of the ultrasound
waves generated by the ultrasound transducer to the
object;
determining, by a liquid level determining arrangement, a
liquid level of the liquid coupling composition in the
fluid basin having the ultrasound transducer positioned
in the fluid basin;
receiving, by an image processing unit, the image dataset
from the imaging device;
receiving, by the image processing unit, a liquid level
signal determined by the liquid level determining
arrangement; and
determining, by the image processing unit, a correction
value for one or more pixel values or voxel values of
the image dataset based on the liquid level signal,
wherein the one or more pixel values or voxel values
generated by the imaging device have been influenced
by the liquid coupling composition.

11. The method of claim 10, wherein the imaging device
is an X-ray device or a Computed Tomography device,
wherein the correction value is configured to compensate
for a truncation artifact, a cupping artifact, a value
offset, or a combination thereof caused by X-ray having
passed through the liquid coupling composition.

12. The method of claim 6, wherein the identified change
in the liquid level is used for confirmation that the registration of the scan by the imaging device remains correct and
the re-registration is performed when the identified change
in the liquid level identifies the inconsistency.

13. The method of claim 6, wherein the breathing cycle of
the object based on the identified change in the liquid level
is determined and the determined breathing cycle is used for
the motion-compensated histotripsy treatment.

14. The method of claim 6, wherein the deformation force
exerted by the fluid basin and the ultrasound transducer onto
the object based on the identified change in the liquid level
is calculated and the deformation on the inner soft tissue
anatomy of the object based on the calculated deformation
force is estimated.

15. A method for image-based guidance of an ultrasound
intervention, the method comprising:
generating, by an imaging device, an image dataset of an
object of the ultrasound intervention;
generating ultrasound waves by an ultrasound transducer
positioned in a fluid basin comprising a liquid coupling
composition, wherein the liquid coupling composition
is provided to assist in a transmission of the ultrasound
waves generated by the ultrasound transducer to the
object;
determining, by a liquid level determining arrangement, a
liquid level of the liquid coupling composition in the
fluid basin having the ultrasound transducer positioned
in the fluid basin;
adjusting a depth of the ultrasound transducer within the
fluid basin, wherein the ultrasound transducer is affixed
to and controlled by a robot; and
determining, by the liquid level determining arrangement,
a position of the ultrasound transducer positioned
within the fluid basin based on: (1) a known position of
the fluid basin, and (2) a change in the liquid level of
the liquid coupling composition caused by the adjusting of the depth of the ultrasound transducer.

16. A method for image-based guidance of an ultrasound
intervention, the method comprising:
generating, by an imaging device, an image dataset of an
object of the ultrasound intervention;
generating ultrasound waves by an ultrasound transducer
positioned in a fluid basin comprising a liquid coupling
composition, wherein the liquid coupling composition
is provided to assist in a transmission of the ultrasound
waves generated by the ultrasound transducer to the
object;
determining, by a liquid level determining arrangement, a
liquid level of the liquid coupling composition in the
fluid basin having the ultrasound transducer positioned
in the fluid basin; and
determining a truncation or cupping correction model
using the determined liquid level in the fluid basin.

17. A method for image-based guidance of an ultrasound
intervention, the method comprising:
generating, by an imaging device, an image dataset of an
object of the ultrasound intervention;
generating ultrasound waves by an ultrasound transducer
positioned in a fluid basin comprising a liquid coupling
composition, wherein the liquid coupling composition
is provided to assist in a transmission of the ultrasound
waves generated by the ultrasound transducer to the
object;

determining, by a liquid level determining arrangement, a liquid level of the liquid coupling composition in the fluid basin having the ultrasound transducer positioned in the fluid basin; and detecting, by the liquid level determining arrangement, a movement of the fluid basin between the generating of the image dataset and the generating of the ultrasound waves.

18. A method for image-based guidance of an ultrasound intervention, the method comprising:

loading a pre-interventional dataset of an object without a fluid basin or with an empty fluid basin having no liquid;

calculating virtual projection images using the pre-interventional dataset;

comparing attenuation of rays in current projection images to virtual projection rays of the virtual projection images;

determining a delta attenuation per projection ray;

determining a fluid filling level of the fluid basin by fitting the delta attenuation of multiple projection rays to a position of the fluid basin; and performing a truncation or cupping artifact compensated computed tomography image reconstruction taking into account the position and fluid filling level of the fluid basin.

19. A method for image-based guidance of an ultrasound intervention, the method comprising:

performing multiple preliminary computed tomography reconstructions assuming different fluid filling levels in a fluid basin positioned on a surface of an object of the ultrasound intervention;

determining a level of a cupping or truncation artifact by: comparing voxel values of known and segmented tissue regions and calculating differences across an image, or determining a strength of global image brightness variations and shapes caused by the cupping or the truncation artifact;

iteratively determining a fluid filling level in the fluid basin with lowest appearance of artifacts or voxel value differences of reference objects across the image; and performing a truncation or cupping artifact compensated computed tomography image reconstruction taking into account a position of the fluid basin and the fluid filling level of the fluid basin.

\* \* \* \* \*